(12) United States Patent
Unali

(10) Patent No.: US 9,144,540 B2
(45) Date of Patent: Sep. 29, 2015

(54) STRUCTURED AQUEOUS SURFACTANT SYSTEMS

(75) Inventor: Giovanni Francesco Unali, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 53 days.

(21) Appl. No.: 14/009,273

(22) PCT Filed: Mar. 2, 2012

(86) PCT No.: PCT/EP2012/053612
§ 371 (c)(1),
(2), (4) Date: Oct. 1, 2013

(87) PCT Pub. No.: WO2012/139818
PCT Pub. Date: Oct. 18, 2012

(65) Prior Publication Data
US 2014/0142202 A1    May 22, 2014

(30) Foreign Application Priority Data
Apr. 12, 2011    (EP) .................................... 11162005

(51) Int. Cl.
*A61K 8/73* (2006.01)
*B01F 17/00* (2006.01)
*C11D 17/00* (2006.01)
*A61K 8/86* (2006.01)
*A61Q 19/10* (2006.01)
*A61Q 5/00* (2006.01)
*A61Q 19/00* (2006.01)

(52) U.S. Cl.
CPC . *A61K 8/731* (2013.01); *A61K 8/86* (2013.01); *A61Q 5/00* (2013.01); *A61Q 19/00* (2013.01); *A61Q 19/10* (2013.01); *B01F 17/0028* (2013.01); *C11D 17/0026* (2013.01)

(58) Field of Classification Search
CPC ...................................................... A61K 8/731
USPC ......................................... 514/781; 510/337
See application file for complete search history.

(56) References Cited

U.S. PATENT DOCUMENTS

| 5,437,810 | A | * | 8/1995 | Ewbank et al. ................ 510/328 |
| 5,653,970 | A | | 8/1997 | Vermeer |
| 6,482,422 | B1 | * | 11/2002 | Paul et al. ...................... 424/402 |
| 6,534,071 | B1 | * | 3/2003 | Tournilhac et al. ........... 424/401 |
| 2002/0065328 | A1 | * | 5/2002 | Dederen et al. .................... 516/9 |
| 2004/0029977 | A1 | | 2/2004 | Kawa et al. |
| 2011/0268681 | A1 | * | 11/2011 | Gonzalez et al. ............ 424/70.1 |

FOREIGN PATENT DOCUMENTS

| EP | 1057477 A1 | 12/2000 |
| JP | 2009-209217 | 9/2009 |
| JP | 2009209217 | 9/2009 |
| WO | WO2010076292 A1 | 7/2010 |
| WO | WO 2010076292 A1 * | 7/2010 |

OTHER PUBLICATIONS

Hoffman et al., "Surfactant Gels, Current Opinion in Colloid and Interface Science", Dec. 1996, vol. 1, No. 6, pp. 726-739.
PCT International Search Report in PCT application PCT/EP2012/053612 dated May 7, 2012 with Written Opinion.
European Search Report in EP application EP 11 16 2005 dated Sep. 16, 2011 with Written Opinion.
PCT International Search Report in PCT application PCT/EP2012/053611 dated Oct. 24, 2012 with Written Opinion.
European Search Report in EP application EP 11 16 2004 dated Sep. 7, 2011 with Written Opinion.
Co-pending Application: Applicant: Smith et al., U.S. Appl. 14/009,258, filed Oct. 1, 2013.
IPRP1 in PCTEP2012053611, Oct. 24, 2013.
IPRP1 in PCTEP2012053612, Oct. 24, 2013.

* cited by examiner

*Primary Examiner* — Nicole M Buie-Hatcher
*Assistant Examiner* — M. Reza Asdjodi
(74) *Attorney, Agent, or Firm* — Greenberg Traurig, LLP

(57) ABSTRACT

The invention provides a structured aqueous surfactant system comprising: a) at least 0.1 wt % nonionic surfactant which is a polyoxyethylene nonionic surfactant having a hydrophilic head group with at least four oxyethylene units; b) from 0.5 to 5 wt % dispersed modified cellulose biopolymer, wherein the modification consists of the cellulose having its C6 primary alcohols oxidized to carboxyl moieties (acid/COOH—) on 10 to 70% of the glucose units and substantially all the remainder of the C6 positions occupied by unmodified primary alcohols; c) from 0 to 10 wt % non-surfactant electrolyte, and d) water.

2 Claims, No Drawings

STRUCTURED AQUEOUS SURFACTANT SYSTEMS

This invention relates to structured aqueous surfactant systems comprising modified cellulose and surfactant.

BACKGROUND

Cellulose is a plentiful, and consequently inexpensive, biopolymer. However, in its unmodified form it is completely insoluble and cannot be dispersed into an aqueous liquid composition to achieve a stable, thickened, product.

Partially and selectively oxidising cellulose at the C6 position creates cellouronates or cellouronic acids which are more water dispersible than cellulose but still relatively insoluble.

WO 2010/076292 describes how this type of oxidised cellulose may be used as an alternative structurant for aqueous detergent compositions. This enables the formulator to replace surfactant required for structuring with relatively low concentrations of low cost, partially oxidised, dispersed modified cellulose. These reduced surfactant compositions nonetheless maintain a thick gel-like consistency which allows suspension of solids or gases, such as bubbles, capsules or beads. According to WO2010/076292, in order to provide gelled material it is essential to use anionic or zwitterionic surfactants. The use of a nonionic surfactant (sorbitan trioleate) does not result in a gel.

Surprisingly, we have now found that certain nonionic surfactants are capable of gelling with the oxidised cellulose described in WO2010/076292, even in the absence of any anionic or zwitterionic surfactant.

SUMMARY OF THE INVENTION

According to a first aspect of the present invention there is provided a structured aqueous surfactant system comprising:
a) at least 0.1 wt % nonionic surfactant which is a polyoxyethylene nonionic surfactant having a hydrophilic head group with at least four oxyethylene units;
b) from 0.5 to 5 wt % dispersed modified cellulose biopolymer, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols;
c) 0 to 10 wt % non-surfactant electrolyte, and
d) water.

Also, according to a second aspect of the invention, there is provided a process to manufacture a structured aqueous surfactant system according to the first aspect, the process comprising the steps of:
(i) dispersing 0.5 to 5 wt % modified cellulose biopolymer in water under high shear to hydrate it, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols;
(ii) adding to this aqueous dispersion at least 0.1 wt % nonionic surfactant which is a polyoxyethylene nonionic surfactant having a hydrophilic head group with at least four oxyethylene units, and
(iii) optionally also adding up to 10 wt % non-surfactant electrolyte consisting of low molecular weight salt,

DETAILED DESCRIPTION OF THE INVENTION

Modified Cellulose Biopolymer

The surfactant system of the present invention comprises from 0.5 to 5 wt % dispersed modified cellulose biopolymer, wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols.

The modified cellulose biopolymer for use in the invention may be characterised as a water insoluble, water dispersible modified cellulose in which only a proportion of its C6 primary alcohol groups have been oxidised to acid groups. Cellulose where all such alcohols have been oxidised is called polyuronic acid or polyglucuronic acid. Such fully oxidised material is soluble in water. It is unsuitable for use in the present invention for two reasons. Firstly, the cost of the extra processing required to create more than 70% substitution of primary alcohols by carboxylic acid groups makes it not cost effective as a replacement for surfactant and second the highly oxidised material tends to include unwanted depolymerised cellulose, which leads to a reduction of yield of insoluble dispersible structurant.

In the context of the present invention, a modified cellulose biopolymer is said to be water soluble, if it leaves less than 10 wt % of its dry mass as undissolved residue when a 2 g dry sample is added to 1 liter of agitated demineralised water at 25° C.

Totally unoxidised (unmodified) cellulose is unable to function as a structurant. Oxidising the cellulose to have at least 10% of the primary alcohols converted to carboxylic acids makes the cellulose dispersible in water and when mixed within the surfactant system the resulting structured liquid or gel maintains the cellulose in a dispersed state so it does not settle over time.

The Cellulose Starting Material

Several factors influence the choice of a suitable starting material.

More porous unmodified cellulosic material will oxidise more rapidly. Characterisation of surface area or porosity is readily achieved by porosimetry or BET measurements. In general, those starting materials that oxidise more rapidly due to their low crystallinity and higher surface area and/or porosity, prove easier to disperse than those that oxidise less rapidly.

The rate of oxidation is also affected by the dimensions of the particles of cellulose starting material; the reduction in rate for longer (>500 micron) fibres is significant. Fibres less than 500 microns long are therefore preferred for this reason and due to the added difficulty in agitation of the longer fibres. While oxidation results in significant gross particle size reduction, this does not compensate for decreased fibril surface accessibility in the long fibres.

Celluloses that have not been previously subjected to acid hydrolysis are a preferred starting material, due to reactivity, cost and resultant product dispersibility.

Relatively unrefined α-cellulose, for example filter aid fibres, provides one of the most readily oxidised and dispersed sources of cellulose. Advantageously, the oxidation process also serves to bleach coloured components, such as lignin, in such unbleached cellulose starting materials. This then renders such materials more suitable for use in contexts where visual clarity of the end product is desirable, for example transparent personal care formulations.

Oxidation

Because of its known specificity for primary alcohol oxidation TEMPO-mediated oxidation of cellulose is preferred (i.e. 2,2,6,6-tetramethylpiperidine-1-oxyl and related nitroxy radical species). The process proceeds well without cooling, at relatively high weight % cellulose in the initial suspension. Simple workup procedures afford clean material suitable for dispersion. Such TEMPO mediated oxidation of cellulose is described in the published literature and the skilled worker will be able as a matter of routine to adapt known methods to achieve the oxidation required by this invention.

While aqueous NaOCl/TEMPO/NaBr is a highly preferred oxidation system, there are a number of other systems available to the skilled worker, especially for large scale production. Among such systems, there may be mentioned use of peracetic acid or monoperoxysulfate salts (Oxone®) as the oxidant with 4-acetamido-2,2,6,6-tetramethylpiperidine-1-oxyl (4-acetamido-TEMPO) as the radical transfer catalyst or mediator and sodium bromide co-catalyst for the oxidation. Elimination of chlorine from the oxidation system is environmentally desirable.

The use of 4-acetamido-TEMPO as radical transfer catalyst is also advantageous as, although it has a higher molecular weight than TEMPO, it has significantly lower vapour pressure reducing potential exposure hazards. Many other 4-substituted TEMPO analogues exist, but many, such as 4-hydroxy-TEMPO exhibit poor stability. TEMPO on solid supports or on soluble polymers may be used.

Electrochemical oxidation is a potentially clean means of effecting oxidation of carbohydrate moieties, although mediation by a radical transfer catalyst (such as TEMPO) is still required.

Laccase mediated oxidation, which also requires a radical transfer catalyst (e.g. TEMPO) but replaces the oxidant with an enzyme, may advantageously be used.

Using the TEMPO system the degree of reproducibility of oxidation of cellulose from the same source is good.

Degree of Oxidation

In the context of the present invention, the term "degree of oxidation" of the modified cellulose means the percentage glucose units oxidised to carboxylic acid as measured by titration with sodium hydroxide. It is assumed that all oxidation takes place at the primary alcohol positions. A reasonable assumption, given that primary alcohol specific oxidation chemistry is employed. Furthermore it is assumed that all oxidation leads to carboxylic acid formation.

Degree of polymerisation (DP) does not seem greatly to influence the performance of the modified cellulose. The key thing is that the modified cellulose must remain insoluble.

During oxidation, there is some degradation of the cellulose allowing release of polymer chains. It is particularly advantageous to keep this to a minimum in order to increase the yield of the modified insoluble cellulose material suitable for structuring applications. We have determined that above 70% oxidisation, the yield is unacceptably low and the processing costs become unacceptably high.

The degree of oxidation of the modified cellulose lies in the range 10 to 70%. As the degree of oxidation increases, the amount of soluble material produced will rise and this reduces the yield of insoluble structuring material, thus the higher degrees of oxidation confer no real structuring benefits. For this reason, it is preferred to restrict the degree of oxidation to 60%, or even 50% and the most preferred modified materials have degrees of oxidation even lower than 40% or sometimes even lower than 30%.

To achieve a high enough dispersibility/solubility for the modified cellulose to act as a structurant it must be oxidised to at least 10%. The exact amount of oxidation required for a minimum effect will vary according to the starting material used. Preferably, it is at least 15% oxidised and most preferably, at least 20% oxidised.

Dispersal of the Modified Cellulose

At small scale, high energy sonication is the preferred method to give the high shear necessary to achieve the aqueous dispersion of the modified cellulose. However, other techniques are more suitable for large scale applications. These include the use of a high speed and high shear stirrer, or a blender, or a homogeniser. Homogenisation may achieve higher levels of dispersed material than are attainable via sonication.

When degrees of oxidation of less than 10% are used, the partially oxidised cellulose proves too resistant to dispersion to produce a transparent or translucent mixture and higher energy input is required. Provided the lower limit of 10% is exceeded, those modified celluloses with a lesser degree of oxidation appear to provide greater structuring capacity once dispersed. This is attributed to less degradation of the material during oxidation and thus the existence of longer individual dispersed (not dissolved) fibrils. This may be because the structure of the cellulose starting material is partially retained, but the fibrils are rendered dispersible by the introduction of negatively charged functional groups on the surface during oxidation.

Oxidised, dispersed cellulose is a largely insoluble polymer that occurs in the form of well dispersed fibrils rather than isolated solvated polymer chains. The fibrils have a large aspect ratio and are thin enough to provide almost transparent dispersions. Carboxylate groups provide anionic surface charge, which results in a degree of repulsion between fibrils, militating against their reassociation into larger structures. Addition of acid to dispersions of oxidised cellulose results in separation of gelled material while at pH between ca 5-9 fibrils may be maintained in a dispersed form as the COO— salt of an appropriate counterion.

Once the high shear dispersion of the modified cellulose has taken place, the remaining process steps can take place in a conventional stirred tank, at relatively low shear. This allows the formulator to make a stock of aqueous dispersion of the modified cellulose, with further ingredients added as and when necessary to enable easy late-stage variations in composition before products are packaged.

The amount of modified cellulose biopolymer in the surfactant system of the invention preferably ranges from 1 to 2 wt % (by total weight modified cellulose biopolymer based on the total weight of the emulsion).

Polyoxyethylene Nonionic Surfactant

The surfactant system of the present invention comprises at least 0.1 wt % nonionic surfactant which is a polyoxyethylene nonionic surfactant having a hydrophilic head group with at least four oxyethylene units (hereinafter termed a "polyoxyethylene nonionic surfactant").

Preferred examples of such materials include polyoxyethylene ethers of fatty alcohols, acids and amides, having from 8 to 20 carbon atoms in the fatty chain and from 4 to about 100 oxyethylene units. Particularly preferred examples of such materials include the condensation products of aliphatic ($C_8$ to $C_{18}$) primary or secondary, saturated or unsaturated, linear or branched chain alcohols with ethylene oxide and having from 4 to 30 ethylene oxide groups. These include, for example, $C_8$ to $C_{15}$ primary or secondary alcohols or mixtures thereof, condensed with from 4 to 30 moles of ethylene oxide. Specific examples include polyoxyethylene (23) lauryl ether (laureth-23), polyoxyethylene (10) lauryl ether (laureth-10), polyoxyethylene (5) lauryl ether (laureth-5) and polyoxyethylene (4) caprylyl ether (capryleth-4), and mixtures thereof.

Other examples of suitable nonionic surfactants for use in the invention include the condensates of from 4 to 80 moles of ethylene oxide with fatty acid partial esters of sorbitan, in which the fatty acid has from 8 to 20 carbon atoms in the fatty chain and may be saturated or unsaturated, linear or branched. These include, for example, condensates of from 4 to 20 moles of ethylene oxide with sorbitan monoesters of $C_{12}$ to $C_{18}$ fatty acids such as lauric acid, stearic acid, palmitic acid and oleic acid. A specific example is polyoxyethylene (20) sorbitan monolaurate.

Mixtures of any of the above described materials may also be used.

Surprisingly, we have observed that gelling behaviour is not critically dependent on the levels of the above nonionic surfactants. This is in contrast to the anionic surfactant based systems described in WO2010/076292 in which viscosity peaks at a certain level of anionic surfactant (around 3 to 5 wt %) and then falls again. Accordingly, a specific advantage of the present invention is that it extends the formulation "window" available to the formulator and therefore the formulation flexibility.

The amount of polyoxyethylene nonionic surfactant in the surfactant system of the invention generally ranges from about 0.2% to about 40%, and preferably ranges from about 1 to 15 wt %, more preferably from about 2 to 12 wt % (by total weight polyoxyethylene nonionic surfactant based on the total weight of the surfactant system).

Other Surfactants

In the system of the invention, it is not necessary to use any anionic surfactants in order to provide gelled material. This may be advantageous, for example in formulations designed for topical skin application, or other contexts where skin mildness is particularly desirable.

Accordingly, a preferred surfactant system according to the invention comprises less than 0.2 wt % anionic surfactant (by total weight anionic surfactant based on the total weight of the surfactant system). More preferably such a surfactant system is substantially free of anionic surfactant. The term "substantially free" in this particular context generally means that the surfactant system comprises less than 0.1%, more preferably less than 0.01%, most preferably less than 0.001% by total weight anionic surfactant based on the total weight of the surfactant system.

However, for other applications, for example where a higher surfactant active level is desired, other surfactants may optionally be included as co-surfactants, i.e. in addition to the polyoxyethylene nonionic surfactant as defined above.

Examples of optional co-surfactants include:
nonionic surfactants that do not have a polyoxyethylene group. Examples of such materials (hereinafter termed "nonionic co-surfactants") include fatty acids and fatty acid esters, ethers, hemi-acetals or acetals of polyhydroxylic compounds or a fatty acid amide which is N-substituted with the residue of a polyhydroxylic compound.

Suitable fatty acids include those of formula $R^1$—COOH, where $R^1$ is a $C_8$ to $C_{24}$, preferably a $C_{12}$ to $_{22}$ hydrocarbyl, preferably alkyl or alkenyl, group. An example is coconut fatty acid.

Suitable esters of polyhydroxylic compounds include saccharide esters, and particularly mono- and/or diesters of fatty acids (as defined above) with a sugar, especially sucrose, fructose, glucose and/or alkylglucose (e.g. methylglucose or ethylglucose). Commercially available sugar esters are usually mixtures containing mono-ester, higher esters and sometimes free starting material (sugar). Examples include glucose palmitate, methylglucose isostearate, methylglucose laurate, methylglucose sesquistearate (mixture of the mono- and diesters), alkylglucose palmitates such as methylglucose or ethylglucose palmitate, methyl glucose dioleate, methyl glucose sesquiisostearate, sucrose palmitate, sucrose stearate and sucrose monolaurate.

Also suitable are polyglyceryl ethers of the above-described sugar esters, such as polyglyceryl-3 methylglucose distearate (a diester of stearic acid and the condensation product of methylglucose and polyglycerin-3).

Other suitable esters of polyhydroxylic compounds include esters of fatty acids, particularly fatty acids having from 8 to 24, preferably 12 to 22, more preferably 16 to 20 carbon atoms, and polyols, particularly glycerol, or a polyglycerol, or an anhydrosaccharide such as sorbitan. Examples include glyceryl monolaurate, glyceryl monooleate, glyceryl monolinoleate, glyceryl monostearate, glyceryl monoisostearate, glyceryl trioctanoate, glyceryl triisostearate, polyglyceryl-3 stearate, polyglyceryl-3 cocoate, sorbitan monooleate, sorbitan monostearate, sorbitan monolaurate, and sorbitan monopalmitate.

Suitable ethers of polyhydroxylic compounds include alkyl polysaccharides of the formula: $R^1$—O-$(G)_a$, where $R^1$ is as defined above for fatty acids; each G is independently a saccharide residue, preferably a glucose residue and a is from 1 to about 5. Examples include decylglucoside, caprylyl/capryl glucoside, laurylglucoside, cocoglucoside, cetostearyl glucoside, arachidyl glucoside, and cocoylethylglucoside.

Another suitable type of nonionic co-surfactant includes fatty acid esters of hydroxycarboxylic acids, in which the fatty acid typically has from 8 to 24, preferably from 12 to 22, more preferably from 16 to 20 carbon atoms and the hydroxycarboxylic acid is preferably citric acid.

Another suitable type of nonionic co-surfactant includes N-substituted fatty acid amides in which the N-substituent is the residue of a polyhydroxylic compound, for example a saccharide residue such as a glucosyl group. This type of emulsifier typically has the formula: $R^1$—CO—$NR^5R^6$, where $R^1$ is as defined above for fatty acids; $R^5$ is a hydrogen atom, a $C_1$ to $C_6$ alkyl group or a group of the formula $R^6$; and $R^6$ is a polyhydroxyl hydrocarbyl group, particularly a group containing from 3 to 10 carbon atoms and 2 to 6 hydroxyl groups, preferably a glucosyl residue.

Mixtures of any of the above described materials may also be used.

The amount of nonionic co-surfactant in the surfactant system of the invention generally ranges from 0 to 10 wt %, and when used, preferably ranges from 1 to 5 wt % (by total weight nonionic co-surfactant based on the total weight of the emulsion).

anionic surfactants. Examples of such materials include sodium lauroyl sarcosinate, sodium lauroyl lactylate, sodium cocoyl glutamate, disodium polyglucose sulfosuccinate/citrate, sodium lauryl ether sulphate (1-3 EO).

Other examples of suitable anionic surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical types of anionic surfactants include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Mixtures of any of the foregoing anionic surfactants may also be used.

The amount of anionic co-surfactant in the surfactant system of the invention generally ranges from 0 to 15 wt %, and when used, preferably ranges from 0.1 to 10% by total weight anionic surfactant based on the total weight of the surfactant system.

amphoteric surfactants. Examples of such materials include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

Typical types of amphoteric surfactants include lauryl amine oxide, cocodimethyl sulphopropyl betaine, lauryl betaine, cocamidopropyl betaines, olivamidopropyl betaines and sodium cocoamphoacetate.

Mixtures of any of the foregoing amphoteric surfactants may also be suitable.

The amount of amphoteric co-surfactant in the surfactant system of the invention generally ranges from 0 to 10%, and when used, preferably ranges from 1 to 5% by total weight amphoteric surfactant based on the total weight of the surfactant system.

Mixtures of any of the above described optional co-surfactants may also used.

Optional Non-Surfactant Electrolyte

The non-surfactant electrolyte is optional. The preferred non-surfactant electrolyte is a water soluble inorganic or organic salt with a molecular weight of less than 500. The electrolyte preferably has a monovalent cation, however at low (less than 2 wt %) levels salts with divalent cations, such as calcium chloride, may be used.

Sodium chloride is the preferred non-surfactant electrolyte.

The amount of non-surfactant electrolyte (such as sodium chloride) in the surfactant system of the invention generally ranges from 0 to 5 wt %, and preferably ranges from 0 to 2 wt % (by total weight non-surfactant electrolyte based on the total weight of the surfactant system).

Formulations

The structured aqueous surfactant system of the invention may advantageously be formulated into a home or personal care composition, such as a skin or hair care composition. Such compositions will generally contain further ingredients to enhance performance and/or consumer acceptability.

Accordingly, other ingredients typically found in home or personal care compositions may be incorporated in the structured aqueous surfactant system according to the invention. The total amount of such additives will not normally exceed 15 wt %. The balance of the composition is water.

Adding small amounts of perfume does not destabilise the structured aqueous surfactant system according to the invention. Furthermore, perfume encapsulates, small beads, free emulsions and even air bubbles stay suspended when dispersed at low shear in the structured aqueous surfactant system.

If too much water is added to the structured aqueous surfactant system of the invention, there is an eventual loss of structuring, but provided the respective concentrations of modified cellulose biopolymer and polyoxyethylene nonionic surfactant are kept above the lower limits of the invention as specified above the structuring is maintained.

Skin or hair care actives may be included to provide skin or hair benefits in addition to cleansing. Examples of such benefits include hydration, nutrition, softness, protection and revitalisation.

Examples of typical skin or hair actives include glycerine, sorbitol, vitamins, botanical extracts, fruit extracts, sugar derivatives, alpha hydroxy acids, isopropyl myristate, UV filters, fatty acids and their esters, silicones, amino acids, hydrolysed proteins, cationic surfactants, essential oils, vegetable oils, mineral oils, sterols, cationic polymers, exfoliating agents and bactericides.

Other optional ingredients include dyes and pigments, pH adjusting agents, additional suspending agents, pearlescers or opacifiers, viscosity modifiers and preservatives.

The above optional ingredients will generally be present individually in an amount ranging from 0 to 5% by weight individual ingredient based on the total weight of the final composition.

The invention is further illustrated with reference to the following, non-limiting examples.

EXAMPLES

Examples 1-25

Various polyoxyethylene nonionic surfactants were added to sonicated dispersions of modified cellulose samples, with differing degrees of oxidation, which were prepared by the method as described in WO2010/076292. No extra electrolyte was added.

Results are given in Tables 1 to 5.

TABLE 1

| Ingredient | Example 1 (% w/w) | Example 2 (% w/w) | Example 3 (% w/w) | Example 4 (% w/w) | Example 5 (% w/w) |
|---|---|---|---|---|---|
| Modified cellulose[1] | 1.3 | 1.3 | 1.3 | 1.3 | 1.3 |
| Polyoxyethylene (20) sorbitan monolaurate | 3 | — | — | — | — |
| Polyoxyethylene (23) lauryl ether | — | 3 | — | — | — |
| Polyoxyethylene (10) lauryl ether | — | — | 3 | — | — |
| Polyoxyethylene (5) lauryl ether | — | — | — | 3 | — |
| Polyoxyethylene (4) caprylyl ether | — | — | — | — | 3 |
| Water | to 100% | to 100% | to 100% | to 100% | to 100% |
| Rheology | Fluid gel | Fluid gel | Fluid gel | Fluid gel | Fluid gel |

[1]Partially and selectively oxidised cellulose as described in WO2010/076292, degree of oxidation 23%

TABLE 2

| Ingredient | Example 6 (% w/w) | Example 7 (% w/w) | Example 8 (% w/w) | Example 9 (% w/w) | Example 10 (% w/w) |
|---|---|---|---|---|---|
| Modified cellulose[2] | 1.3 | 1.3 | 1.3 | 1.3 | 1.3 |
| Polyoxyethylene (20) sorbitan monolaurate | 3 | — | — | — | — |
| Polyoxyethylene (23) lauryl ether | — | 3 | — | — | — |
| Polyoxyethylene (10) lauryl ether | — | — | 3 | — | — |

TABLE 2-continued

| Ingredient | Example 6 (% w/w) | Example 7 (% w/w) | Example 8 (% w/w) | Example 9 (% w/w) | Example 10 (% w/w) |
|---|---|---|---|---|---|
| Polyoxyethylene (5) lauryl ether | — | — | — | 3 | — |
| Polyoxyethylene (4) caprylyl ether | — | — | — | — | 3 |
| Water | to 100% | to 100% | to 100% | to 100% | to 100% |
| Rheology | Firm gel | Firm gel | Firm gel | Firm gel | Firm gel |

[2]Partially and selectively oxidised cellulose as described in WO2010/076292, degree of oxidation 27.5%

TABLE 3

| Ingredient | Example 11 (% w/w) | Example 12 (% w/w) | Example 13 (% w/w) | Example 14 (% w/w) | Example 15 (% w/w) |
|---|---|---|---|---|---|
| Modified cellulose[3] | 1.3 | 1.3 | 1.3 | 1.3 | 1.3 |
| Polyoxyethylene (20) sorbitan monolaurate | 3 | — | — | — | — |
| Polyoxyethylene (23) lauryl ether | — | 3 | — | — | — |
| Polyoxyethylene (10) lauryl ether | — | — | 3 | — | — |
| Polyoxyethylene (5) lauryl ether | — | — | — | 3 | — |
| Polyoxyethylene (4) caprylyl ether | — | — | — | — | 3 |
| Water | to 100% | to 100% | to 100% | to 100% | to 100% |
| Rheology | Firm gel | Firm gel | Firm gel | Firm gel | Firm gel |

[3]Partially and selectively oxidised cellulose as described in WO2010/076292, degree of oxidation 23.5%

TABLE 4

| Ingredient | Example 16 (% w/w) | Example 17 (% w/w) | Example 18 (% w/w) | Example 19 (% w/w) | Example 20 (% w/w) |
|---|---|---|---|---|---|
| Modified cellulose[2] | 1.3 | 1.3 | 1.3 | 1.3 | 1.3 |
| Polyoxyethylene (20) sorbitan monolaurate | 3 | — | — | — | — |
| Polyoxyethylene (23) lauryl ether | — | 3 | — | — | — |
| Polyoxyethylene (10) lauryl ether | — | — | 3 | — | — |
| Polyoxyethylene (5) lauryl ether | — | — | — | 3 | — |
| Polyoxyethylene (4) caprylyl ether | — | — | — | — | 3 |
| Water | to 100% | to 100% | to 100% | to 100% | to 100% |
| Rheology | Firm gel | Firm gel | Firm gel | Firm gel | Firm gel |

[4]Partially and selectively oxidised cellulose as described in WO2010/076292, degree of oxidation 26.5%

TABLE 5

| Ingredient | Example 16 (% w/w) | Example 17 (% w/w) | Example 18 (% w/w) | Example 19 (% w/w) | Example 20 (% w/w) |
|---|---|---|---|---|---|
| Modified cellulose[5] | 1.3 | 1.3 | 1.3 | 1.3 | 1.3 |
| Polyoxyethylene (20) sorbitan monolaurate | 3 | — | — | — | — |
| Polyoxyethylene (23) lauryl ether | — | 3 | — | — | — |
| Polyoxyethylene (10) lauryl ether | — | — | 3 | — | — |
| Polyoxyethylene (5) lauryl ether | — | — | — | 3 | — |
| Polyoxyethylene (4) caprylyl ether | — | — | — | — | 3 |
| Water | to 100% | to 100% | to 100% | to 100% | to 100% |
| Rheology | Firm gel | Firm gel | Firm gel | Firm gel | Firm gel |

[5]Partially and selectively oxidised cellulose as described in WO2010/076292, degree of oxidation 26%

Examples 26 to 28 and Comparative Example A

A series of surfactant systems were prepared in order to evaluate the formulational benefits of the invention. The ingredients are shown below in Table 6.

TABLE 6

| Ingredient | Comparative Example A (% w/w) | Example 26 (% w/w) | Example 27 (% w/w) | Example 28 (% w/w) |
|---|---|---|---|---|
| Oxidised cellulose[6] | 1 | 1 | 1 | 1 |
| Brij ® 35[7] | — | 5 | 5 | — |
| Sodium lauryl ether sulphate (3EO) | 3 | — | 3 | Total 25% |
| Neodol ® 25-7[8] | — | — | — | |
| Linear alkyl benzene sulphonate (LAS) | — | — | — | |
| Coconut fatty acid | — | — | — | |
| Water | to 100 | To 100 | to 100 | To 100 |

[6]Partially and selectively oxidised cellulose as described in WO2010/076292
[7]Polyoxyethylene (23) lauryl ether
[8]C12-C15 alcohol ethoxylate with 7 moles of ethylene oxide Comparative Example A represents a formulation which is not according to the invention, containing 3 wt % anionic surfactant. We have observed that in this type of system, viscosity falls again beyond about 6 wt % anionic surfactant.

Example 26 represents a formulation according to the invention, containing 5% polyoxyethylene nonionic surfactant. We have observed that viscosity in this type of system does not change significantly as a function of the level of nonionic surfactant.

Example 27 represents a formulation according to the invention, with 8% total surfactant. This shows how the use of polyoxyethylene nonionic surfactant extends the formulation space available to the formulator, since viscosity is maintained despite the increased overall surfactant level.

Example 28 is representative of a commercial concentrated laundry composition. Surprisingly the oxidised cellulose[6] is able to increase the viscosity of this formulation, even though the overall surfactant level is 25 wt %.

The invention claimed is:
1. A structured aqueous surfactant system comprising:
a) at least 0.1 wt % nonionic surfactant;
   wherein the nonionic surfactant is a polyoxyethylene nonionic surfactant having a hydrophilic head group with at least four oxyethylene units;
b) from 0.5 to 5 wt % dispersed modified cellulose biopolymer,
   wherein the modification consists of the cellulose having its C6 primary alcohols oxidised to carboxyl moieties (acid/COOH—) on 10 to 70% of the glucose units and substantially all the remainder of the C6 positions occupied by unmodified primary alcohols;
c) 0 to 10 wt % non-surfactant electrolyte, and
d) water;

wherein the structured aqueous surfactant system is free of anionic and zwitterionic surfactants; and wherein the nonionic surfactant, the biopolymer, the electrolyte and the water are present in sufficient amounts so as to result in the structured aqueous surfactant system that is a gel.

2. The structured aqueous surfactant system according to claim 1, wherein the polyoxyethylene nonionic surfactant is selected from polyoxyethylene ethers of fatty alcohols, acids and amides, having from 8 to 20 carbon atoms in the fatty chain and from 4 to about 100 oxyethylene units.

* * * * *